US007648509B2

(12) United States Patent
Stark

(10) Patent No.: US 7,648,509 B2
(45) Date of Patent: Jan. 19, 2010

(54) SACROILIAC JOINT IMMOBILIZATION

(75) Inventor: John G. Stark, Minnetonka, MN (US)

(73) Assignee: Ilion Medical LLC, Minneapolis, MN (US)

( * ) Notice: Subject to any disclaimer, the term of this patent is extended or adjusted under 35 U.S.C. 154(b) by 267 days.

(21) Appl. No.: 10/797,481

(22) Filed: Mar. 10, 2004

(65) Prior Publication Data

US 2008/0009861 A1    Jan. 10, 2008

Related U.S. Application Data

(60) Provisional application No. 60/453,261, filed on Mar. 10, 2003.

(51) Int. Cl.
*A61B 17/56* (2006.01)
(52) U.S. Cl. ...................................... 606/90
(58) Field of Classification Search ............ 606/72, 606/73, 76, 77, 61–66, 57, 60, 86 R, 90, 86 A, 606/105; 411/393; 408/225; 623/11.11, 623/16.11, 17.11, 18.11, 22.11, 23.39
See application file for complete search history.

(56) References Cited

U.S. PATENT DOCUMENTS

| 4,488,542 | A | * | 12/1984 | Helland | 606/59 |
| 4,569,338 | A | * | 2/1986 | Edwards | 606/61 |
| 4,590,928 | A | * | 5/1986 | Hunt et al. | 128/92 |
| 4,950,270 | A | * | 8/1990 | Bowman et al. | 606/72 |
| 5,242,444 | A | * | 9/1993 | MacMillan | 606/61 |
| 5,334,205 | A | * | 8/1994 | Cain | 606/96 |
| 5,336,225 | A | * | 8/1994 | Zang | 606/73 |
| 5,368,593 | A |   | 11/1994 | Stark | |
| 5,443,509 | A |   | 8/1995 | Boucher et al. | |
| 5,456,267 | A |   | 10/1995 | Stark | |
| 5,669,909 | A |   | 9/1997 | Zdeblick et al. | |
| 5,741,261 | A |   | 4/1998 | Moskovitz et al. | |
| 5,743,914 | A | * | 4/1998 | Skiba | 606/73 |
| 5,772,594 | A | * | 6/1998 | Barrick | 600/407 |
| 5,865,847 | A |   | 2/1999 | Kohrs et al. | |

(Continued)

FOREIGN PATENT DOCUMENTS

WO    WO 95/35180    12/1995

OTHER PUBLICATIONS

Presentation by Dr. John G. Stark, Minnesota Orthopedic Society, Eighteenth Annual Meeting, May 2002.

(Continued)

*Primary Examiner*—Eduardo C Robert
*Assistant Examiner*—David Comstock
(74) *Attorney, Agent, or Firm*—Dardi & Associates, PLLC; Peter S. Dardi; Elizabeth Q. Shipsides

(57) ABSTRACT

Improved tools and procedures relate to the immobilization of the sacroiliac joint for the treatment of pain associated with the joint. Kits comprise, for example, a guide element and an immobilization element of a biocompatible material with a size and shape suitable for placement within the sacroiliac joint. Suitable immobilization elements include, for example, pins, nails, screws, darts, wedges, shims and hardening material. A bioactive agent can be delivered into the joint to compliment the immobilization and promote healing. Suitable procedures can be done in a less invasive procedure through a cannula or the like.

13 Claims, 5 Drawing Sheets

U.S. PATENT DOCUMENTS

| | | | | |
|---|---|---|---|---|
| 5,919,193 A | * | 7/1999 | Slavitt | 606/65 |
| 5,928,239 A | * | 7/1999 | Mirza | 606/79 |
| 5,993,463 A | * | 11/1999 | Truwit | 606/130 |
| 6,053,916 A | * | 4/2000 | Moore | 606/61 |
| 6,175,758 B1 | * | 1/2001 | Kambin | 600/426 |
| 6,283,966 B1 | | 9/2001 | Houfburg | |
| 6,290,724 B1 | | 9/2001 | Marino | |
| 6,306,170 B2 | | 10/2001 | Ray | |
| 6,351,573 B1 | | 2/2002 | Schneider | |
| 6,479,633 B1 | | 11/2002 | Ni et al. | |
| 6,562,049 B1 | | 5/2003 | Norlander et al. | |
| 6,595,995 B2 | | 7/2003 | Zdeblick et al. | |
| 6,607,487 B2 | * | 8/2003 | Chang et al. | 600/437 |
| 6,635,059 B2 | * | 10/2003 | Randall et al. | 606/73 |
| 6,666,888 B1 | | 12/2003 | Jackson | |
| 6,746,451 B2 | * | 6/2004 | Middleton et al. | 606/79 |
| 6,984,235 B2 | | 1/2006 | Huebner | |
| 7,083,647 B1 | | 8/2006 | Sklar et al. | |
| 2002/0087161 A1 | * | 7/2002 | Randall et al. | 606/73 |
| 2002/0099288 A1 | * | 7/2002 | Chang et al. | 600/439 |
| 2002/0183846 A1 | | 12/2002 | Kuslich et al. | |
| 2003/0032098 A1 | | 2/2003 | Young et al. | |
| 2004/0215198 A1 | | 10/2004 | Marnay et al. | |
| 2004/0228901 A1 | * | 11/2004 | Trieu et al. | 424/426 |
| 2004/0267365 A1 | | 12/2004 | Fornari | |
| 2005/0021041 A1 | | 1/2005 | Michelson | |
| 2005/0038513 A1 | | 2/2005 | Michelson | |
| 2006/0058793 A1 | | 3/2006 | Michelson | |
| 2006/0084992 A1 | | 4/2006 | Michelson | |
| 2006/0085068 A1 | | 4/2006 | Barry | |
| 2006/0089646 A1 | | 4/2006 | Bonutti | |
| 2006/0111782 A1 | | 5/2006 | Petersen | |
| 2006/0129238 A1 | | 6/2006 | Paltzer | |
| 2006/0200139 A1 | | 9/2006 | Michelson | |
| 2006/0224240 A1 | | 10/2006 | Allard et al. | |
| 2006/0235522 A1 | | 10/2006 | Foley | |
| 2007/0027543 A1 | | 2/2007 | Gimble et al. | |
| 2007/0032875 A1 | | 2/2007 | Blacklock et al. | |
| 2007/0055374 A1 | | 3/2007 | Copf, Jr. et al. | |
| 2008/0249627 A1 | | 10/2008 | Moehlenbruck et al. | |

OTHER PUBLICATIONS

Wise et al., "Minimally Invasive Sacroiliac Arthrodesis Outcomes of a New Technique" J. Spinal Discord Tech., 21 (8):579-584, (2008).

* cited by examiner

SACROILIAC JOINT IMMOBILIZATION

CROSS REFERENCE TO RELATED APPLICATIONS

This application claims priority to U.S. Provisional Patent Application Ser. No. 60/453,261 to Stark, filed on Mar. 10, 2003, entitled Sacroiliac Joint Immobilization," incorporated herein by reference.

FIELD OF THE INVENTION

The invention relates to approaches for the immobilization or fusion of the Sacroiliac joint and apparatuses for facilitating the procedure. Immobilization may refer to mechanical holding or surgical fusion.

BACKGROUND OF THE INVENTION

Lower back pain is a common ailment among the population and results in both pain and suffering as well as loss of work time. Thus, approaches for the treatment of back pain can both relieve suffering as well as reduce employee down time. Thus, effective treatments for lower back pain have both economic benefits as well as the benefit of alleviating considerable suffering.

The sacroiliac joint is located at the juncture of the ilium, the upper bone of the pelvis, and the sacrum at the base of the spine. While the sacroiliac joint has a limited range of motion, dysfunction of the joint has been identified. The joint is supported by a range of ligaments including, for example, the sacroiliac ligament at the base of the joint and the anterior sacroiliac ligament at the top of the joint.

SUMMARY OF THE INVENTION

In a first aspect, the invention pertains to a kit comprising a guide pin or guide assembly and an immobilization/fusion element. The immobilization element comprises a biocompatible material with a size and shape suitable for placement within the sacroiliac joint of a human patient. In some embodiments, the kit comprises a cutting guide with elements for positioning the cutting guide to align a cutting element within the sacroiliac joint, generally along the axis of the joint, i.e., in the crack of the joint or its extra-articular recess. In some embodiments, the kit can further comprise a drill bit and/or a cannula.

In some embodiments relating to another aspect, the invention pertains to a screw having a thread taper of at least about 1 degrees and appropriate dimensions for implantation into the sacroiliac joint of a human patient. However, the other embodiments, screws and other immobilization elements are contemplated.

In a further aspect, the invention pertains to a method for immobilizing or fusing a patient's sacroiliac joint through a less invasive procedure. The method comprises:

performing an incision suitable for the placement of a cannula or guide pin;

optionally, drilling or forming one or more reaming channels in the sacroiliac joint, generally along the axis of the joint along the crack of the joint, through the cannula;

inserting an immobilization/fusion element into the drilled area of the sacroiliac joint through the cannula; and closing the incision.

In some embodiments, a self-tapping screw can be used, such that drilling or forming reaming channels is not necessary. In some embodiments, the method can further comprise placement of a guide pin through the cannula. The placement of the guide pin can be performed by guiding the placement of the guide pin using a real time image. A plurality of immobilization/fusion elements can be used.

DESCRIPTION OF THE INVENTION

Figure 1:
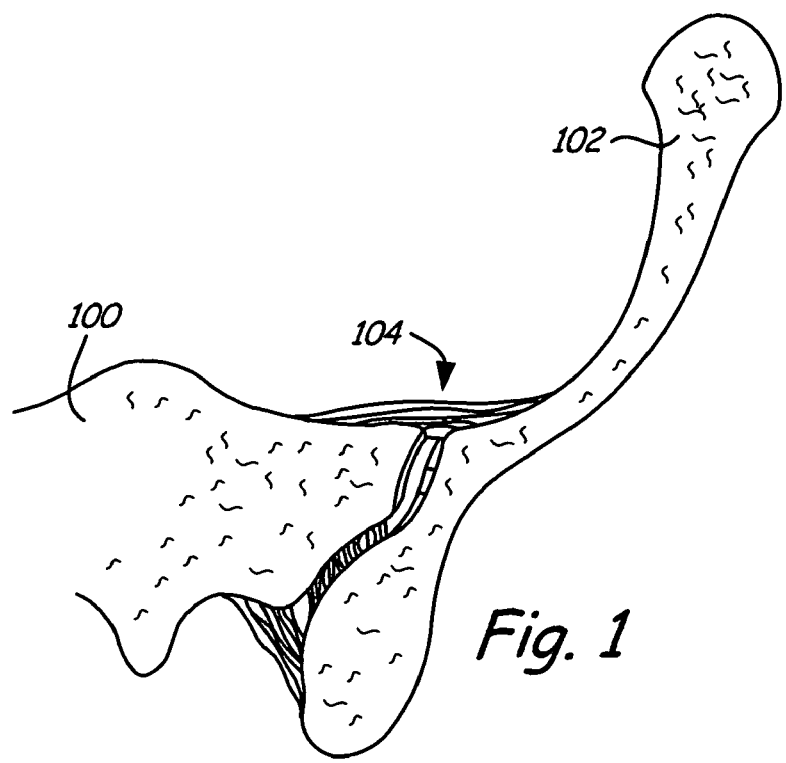
FIG. 1 is a sectional view of the sacroiliac joint.

It has been discovered that immobilization of the sacroiliac joint can result in significant relief of lower back pain. Improved approaches for the immobilization and tools for performing the immobilization of the sacroiliac joint are described herein. In particular, with respect to some embodiments, less invasive procedures can be performed to place implants within the joint to achieve the desired immobilization. Furthermore, kits can include, for example, one or more guide pins, a drill guide, a drill bit and/or insertion material for placement within the joint in contact with adjacent tissue. The insertion material can be, for example, bone graft material, titanium metal fragments, a dart, a shim, a wedge, a pin, a screw, or the like, or combinations thereof. In some embodiments, screws can be used that have non-uniform thread designs. Some immobilization elements can further involve the anchoring of an immobilization cage or the like to facilitate the immobilization. The insertion material can further comprise a biologic agent, such as a stimulating biologic agent. Additional therapeutics can be applied along with the insertion material. For less invasive approaches, the kits can further include, for example, a cannulated device to guide the process and/or appropriate instructions and labeling.

Immobilization of the sacroiliac joint generally involves placement of an immobilization structure within the joint, i.e., between the ilium and the sacrum. While not wanting to be limited by theory, presumably immobilization of the joint reduces or eliminates contact between worn or damaged sections of the joint that result in the pain. Examination of the joint can be used to determine whether immobilization of the joint is indicated. In general, the immobilization can be performed either by performing surgery to expose the appropriate sections of the joint or through less invasive approaches in which the articles are introduced to the region through a cannula with probes or the like. In any case, immobilization of the joint involves identifying appropriate locations to place the immobilization elements. Once the appropriate locations are identified, the locations are exposed and the immobilization elements are appropriately placed. Drilling or cutting may or may not be used to facilitate the placement of the immobilization elements. Cutting guides and/or drill guides can be used in either the open procedures and/or in the less invasive procedures.

For performing the less invasive approaches, cannula can be used to facilitate and guide the procedure while protecting the tissue in the vicinity. Imaging methods can be used to facilitate the procedure. In particular, a small incision can be made into which an orienting probe or pin is inserted. The placement of the cannula can be guided by the probe, and once the cannula is in place, the probe/pin can be removed, cut down or used to guide the placement of an immobilization element, such as a cannulated screw placed over the pin. Additional incisions can be used in the placement of the cannula as appropriate. Furthermore, a plurality of immobilization elements can be inserted either based on a single incision or multiple incisions, which may or may not involve repositioning the cannula. The description of spinal surgical techniques using minimally invasive techniques is described in U.S. Pat. No. 5,741,261 to Moskovitz et al., entitled "Minimally Invasive Spinal Surgical Methods And Instruments, incorporated herein by reference for its general teachings of techniques and instruments for performing less invasive orthopedic procedures.

For either open techniques and/or less invasive techniques, one or more immobilization points can be identified, for example, from an image using x-ray or other imaging technique, based on appropriate positioning of the adjacent bones and appropriate anchoring to effect the immobilization and ligamentotaxis. Once the points are identified, one or more guide pins may or may not be used to mark the immobilization points. If guide pins are used, they can be inserted into position to guide drilling and/or placement of immobilization elements. X-rays can be taken with the guide pins in place to verify proper placement. Also, x-rays and/or other imaging approaches can be used before and/or during pin placement for visual imaging, which can be performed real time. Placement of a guide based on a CT image for back surgery is described in U.S. Pat. No. 6,175,758 to Kambin, entitled "Method For Percutaneous Anthroscopic Disc Removal, Bone Biopsy And Fixation Of th Vertebrae," incorporated herein by reference.

A wide range of immobilization elements is suitable for immobilizing the SI joint either alone or in combination. For example, the immobilization element can be a pin, nail, a screw, a dart, a wedge, a shim, a cage, agglomerated inorganic and/or organic material, or the like or combinations thereof. Pins, nails, screws and the like can be further connected to a plate, a nut, a cage or other connectors or combinations of connectors to further promote immobilization. Screws can be effectively used based anchoring the screw within the joint. Suitable screws can be solid or hollow. The threads of the screw can grip the bone on either side of the joint to further the immobilization of the joint. Thus, screws with sharp and/or pointed threads can be effective. Similarly, a non-uniform thread can improve the gripping while providing for effective implantation of the screw. In some embodiments, a screw can be tapered along the threads by 10 degrees or more to facilitate implantation and/or the gripping function. A self-tapping screw with one or more flutes or the like can be used, such that drilling may not be used.

Implantation elements can be formed, for example, from biocompatible material. Biocompatible metals and/or rigid polymers, for example, can be effectively used. In particular, titanium elements generally yield desirable results for interfacing with bones. Similarly, metal powder, such as powders of titanium or titanium compositions with appropriate particle size, can be formed into composites, for example, with rigid polymers to form desired immobilization elements. In addition, synthetic bone materials and/or sterile bone materials, either allograft or xenograft materials, can be used to form the implantation elements. Suitable synthetic bone material includes, for example, coral and calcium compositions, such as hydroxyapatite, calcium phosphate and calcium sulfite.

The immobilization elements can further comprise one or more biologically active agents that facilitate the stabilization of the immobilized joint. For example, the biologically active agent can be coated onto the exterior of the immobilization element and/or applied for gradual release such as by blending in a bioresorbable polymer that releases the biologically active agent or agents in an appropriate time dependent fashion as the polymer degrades within the patient. Suitable biologically active agents include, for example, bone morphogenic protein (BMP) and cytokines. BMP mediates the formation and healing of bone, cartilage, tendon and other bone related tissues. One human BMP polypeptide is described in detail in Published U.S. Patent Application Serial Number 2003/032098 to Young et al., entitled "Bone Morphogenic Protein," incorporated herein by reference. Similarly, cytokines can be effective to stimulate bone marrow growth. A human cytokine, human chemokine alpha 2, is described in U.S. Pat. No. 6,479,633 to Ni et al., entitled "Chemokine Alpha 2," incorporated herein by reference.

In general, for application to the tools for the performance of the sacroiliac joint immobilization can be distributed in a kit for use by a medical professional. In some embodiments, the kit comprises a guide pin and an immobilization element. The kit can further comprise a cutting guide, a drill guide, taps, distractor, retractor, and/or a drill bit. For less invasive procedures, the kit can comprise a cannula and/or other tools for performing the less invasive procedure, for example, with appropriate imaging techniques.

The improved approaches described herein provide for effective, reproducible, efficient and safe procedures for the immobilization of the SI joint. The procedures are systematic such that less experienced surgeons can effectively perform the procedures with satisfactory outcomes. The use of minimally invasive procedures can provide for more rapid recovery of the patient and a quicker return to normal activity. Kits provide a convenient and efficient approach to the distribution of equipment for the performance of a selected embodiment of the procedure.

Sacroiliac Joint and Immobilization

Figure 2:
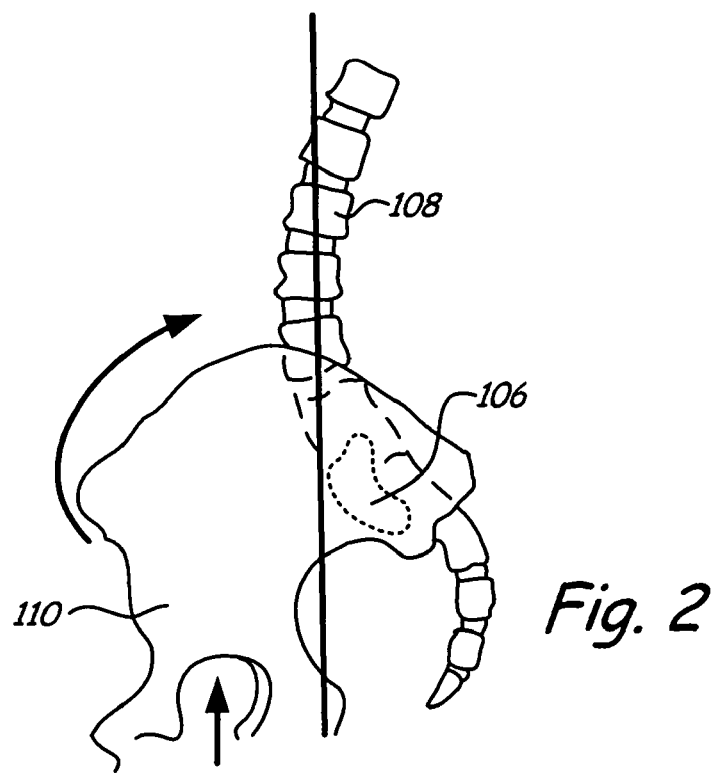
FIG. 2 is a side view of the sacroiliac joint with hidden vertebrae and the sacroiliac joint shown in phantom lines.
Figure 3:
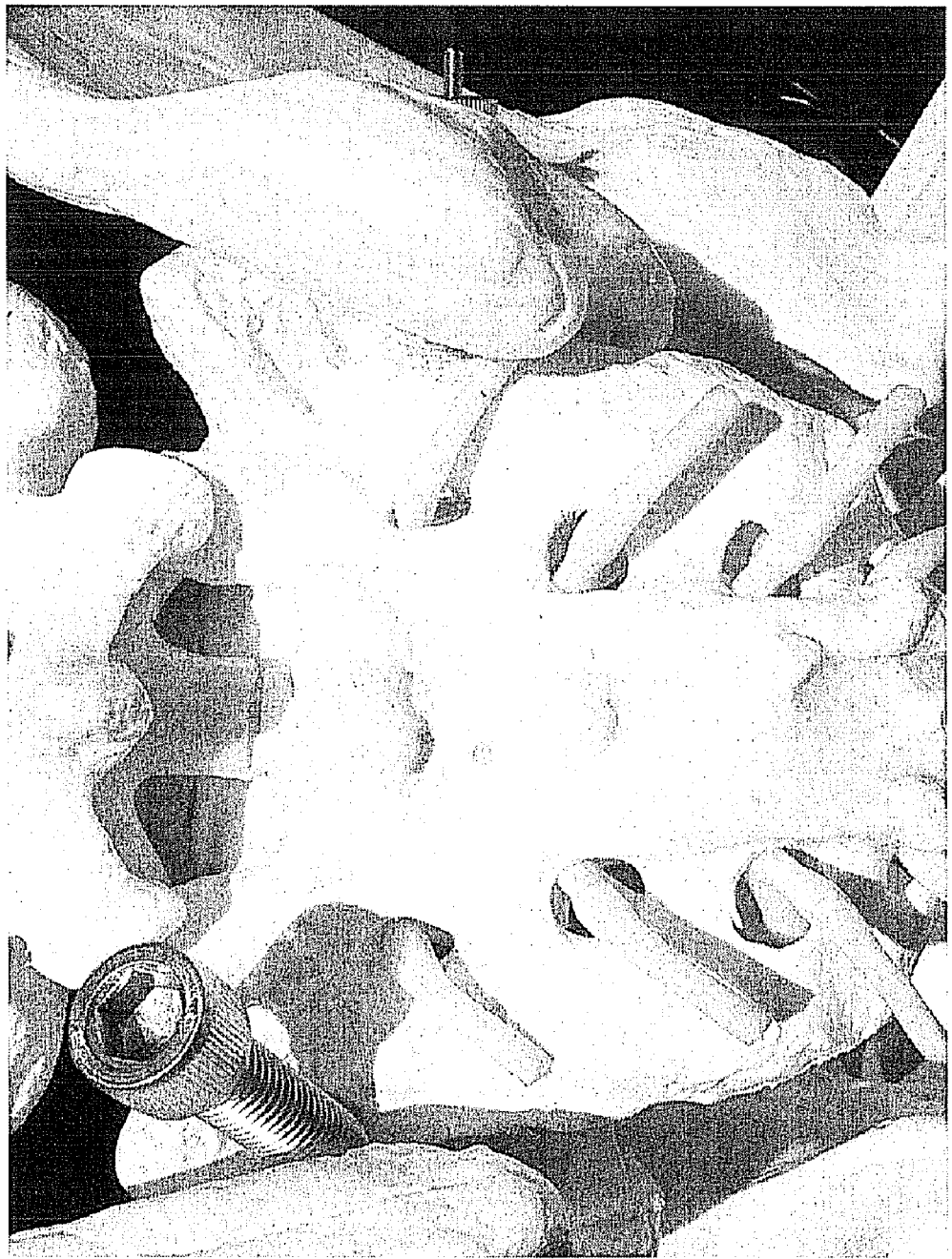
FIG. 3 is a front view of a model of the sacroiliac joint immobilized with a screw.

A portion of the sacroiliac (SI) joint is shown in FIG. 1. As noted above, the SI joint is located between the sacrum 100 at the base of the spin and the ilium 102, the upper bone of the pelvis. As shown in FIG. 1, various ligaments 104 support the joint. Referring to FIG. 2, walking and other movement apply torque on the SI joint 106. As shown in FIG. 2, SI joint 106 is shown with phantom lines between the spine 108 and the pelvis 110. This torque on the SI joint can result in pain if there is injury or disease. Immobilization of the SI joint is shown on a model in FIG. 3 using a screw.

Tools for Sacroiliac Joint Immobilization

In some embodiments of particular interest, the tools for the sacroiliac immobilization are designed to reduce the invasiveness of the procedure. However, some of the improved components, combinations and procedures can be used for more standard procedures as well as in less invasive procedures. Combinations of tools for a particular procedure can be conveniently arranged in a kit such that tools to be used together are available to the physician/health care professional performing the procedure. In addition, the tools can be used to facilitate the delivery of a biological agent to facilitate the beneficial effects of the procedure.

Figure 4:
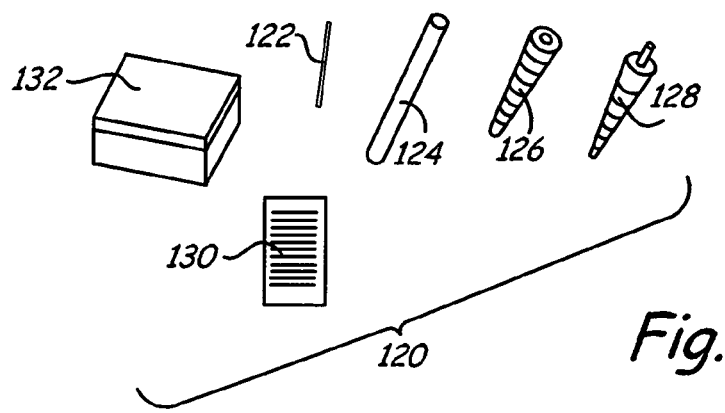
FIG. 4 is a schematic view of a kit with tools for performing an immobilization procedure on the sacroiliac joint.

For the performance of some embodiments of the immobilization procedures, a tool set for the procedure generally comprises a guide component and an immobilization element, optionally along with a cutting element, a cannula and/or a drill bit as well as any other appropriate tools. A kit comprising the collection of tools along with appropriate labels in a container is shown schematically in FIG. 4. Specifically, kit 120, as shown in FIG. 4, comprises a guide component 122, a cannula 124, an immobilization element 126, a cutter/drill bit 128 and instructions 130 with appropriate warnings within container 132. Various other optional components can be included with the kit to facilitate access to the immobilization point, preparation of the immobilization site and/or delivery of the immobilization element.

Figure 5:
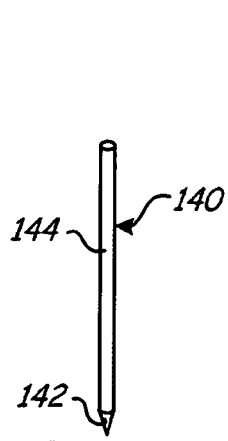
FIG. 5 is a perspective, side view of a guide pin.

Suitable guide components include, for example, a guide pin or the like. The guide element generally may be used in less invasive procedures or in open procedures. Referring to FIG. 5, a guide pin 140 generally includes a point 142 and a shaft 144. Guide pin 140 can be formed from a metal or a metal composite, such as a metal/polymer composite or a metal/ceramic composite, to provide for imaging of pin placement using x-rays or other suitable imaging procedure. Suitable guide pins can be formed from titanium, stainless steel or other biocompatible metals such as various alloys, such as Nitinol®, a nickel-titanium alloy, used in forming implantable medical components. A guide pin can have a circular cross section, oval cross section, rectangular cross section, triangular cross section or other desired shape.

Figure 6:
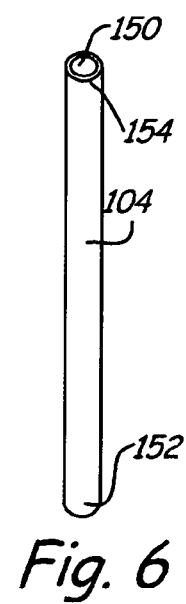
FIG. 6 is a perspective, side view of a cannula.

Cannula 104 forms a passageway for performing the procedure. Referring to FIG. 6, cannula 104 generally includes a central passage 150, a distal end 152 and a proximal end 154. Central passage 150 provides a space for the introduction of appropriate tools to complete the procedure while the walls of the cannula provide protection for the surrounding tissue. The cannula or its distal end can be tapered, and it is the distal end of the cannula that is inserted into the body. The cannula can come in a variety of lengths and exterior and interior surface diameters, dependent on the needs of the devices used for the procedure. The cannula generally has an outer diameter of no more than about 2.5 centimeters (cm), and the wall of the cannula can be as thin as suitable with the device having the desired mechanical strength. The cannula has a sufficient length to reach the SI joint and extend outward from the patient. The cannula can have a circular cross section, oval cross section, rectangular cross section or other desired shape that provides the desired channel. The cross sectional shape and size can vary over the length of the cannula.

The cannula provides the passageway for the placement and insertion of the immobilization element, as well as for performing drilling/cutting or other preparatory work for appropriate embodiments. Introduction of various tools, implants and other devices necessary to immobilize the sacroiliac joint are facilitated through the cannula. Cannulae are typically formed from metals, such as stainless steel, titanium or combinations thereof, metal composites or polymers, such as polyesters.

Figure 7:
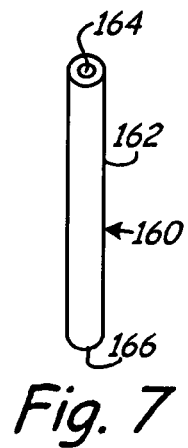
FIG. 7 is a perspective side view of a cannulated trocar.

A trocar can be generally utilized with the cannula. The trocar within the cannula functions as an introducer to get the cannula positioned. A trocar opens a path for the placement of the cannula while reducing trauma to the surrounding tissue. A trocar typically includes a shaft and a tapered tip. Referring to FIG. 7, a trocar 160 is depicted having a shaft 162, a channel 164 and a rounded tip 166. The diameter of the trocar is less than the diameter of the interior passage of the cannula, such that the trocar can fit in the passage during delivery of the cannula. A trocar generally has a tapered distal end that can be rounded or pointed to push through soft tissue. The trocar can be cannulated, i.e., have a central channel, to provide for insertion over a pin or the like, which can guide placement of the trocar and corresponding cannula. Generally, trocars are formed of metal, metal composite material or polymers, and are typically formed of stainless steel or titanium. The trocar is generally longer than the cannula, such that the cannula can extend from the distal end of the cannula during delivery of the cannula while simultaneously extending from the proximal end of the cannula for insertion and removal from the cannula. The shape and size of the trocar is determined by the corresponding shape and size of the inner passage of the cannula. The trocar can have a stop that limits the insertion into the cannula to provide for the desired entension of the trocar from the distal end of the cannula. The use of a trocar for the delivery of a cannula is described further in U.S. Pat. No. 6,562,046 to Sasso, entitled "Screw Delivery System And Method," incorporated herein by reference.

Figure 8:
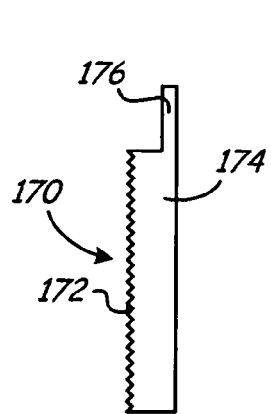
FIG. 8 is a side view of a cutter.
Figure 9:
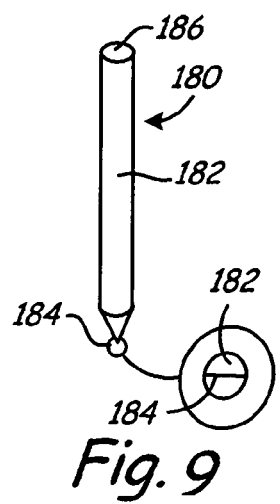
FIG. 9 is a perspective side view of a chisel, in which the insert shows an expanded end view of the tip.
Figure 10:
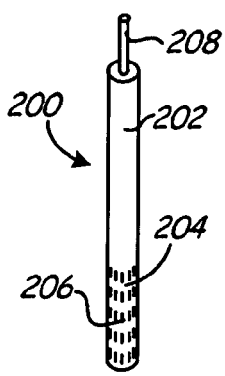
FIG. 10 is a perspective side view of a scrapper.

One or more tools can be used to prepare the SI joint for the placement of the immobilization element. Appropriate preparation tools include, for example, cutters, drills/drill bits, chisels, scrapers or the like. Preparation of the joint can involve opening the joint for the placement of the immobilization element and/or preparation of the bone surface for healing following immobilization. Cutters generally comprise a blade or the like and can be connected to a motorized drive that moves the blade back and forth. Referring to an example embodiment in FIG. 8, cutter 170 has a cutting edge 172 on blade 174 and a chuck 176 for connection to a handle or motorized cutting drive. Cutting edge 172 and blade 174 can be configured for cutting bone. Referring to FIG. 9, a chisel 180 generally has a shaft 182, a chisel edge 184 (shown in an end view in the insert), and a contact surface 186. A mallet or the like of the like can be used to hammer on the contact surface to cut with the chisel. An example of a scraper 200 is shown in FIG. 10. Scraper 200 has a shaft 202, a scraping surface 204 with sharp protrusions 206 and a handle or chuck 208 for attachment to a handle or the like. Generally, cutting blades, drill bits, chisels and scrapers are formed from suitable metals, such as stainless steel and titanium, although some other hard materials can be used. The cutting elements (e.g., blades, drill bits, chisels or scrapers) have an appropriate dimension to prepare the joint for placement of the immobilization element. For less invasive procedures, the elements have a suitable dimension for use through the cannula. In these embodiments, the diameters of the elements are generally no more than about 2 cm. A drill guide or cutting guide can be used to guide the preparation process. The drill guide/cutting guide generally comprises a positioning element that orients the drill guide for appropriate placement to guide the drilling/cutting. The drill guide/cutting guide generally further comprises a guide element that guides the drill bit/cutting blade with the guide in appropriate position.

Figure 11:
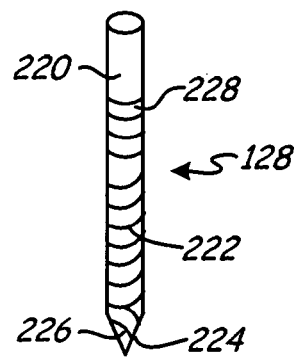
FIG. 11 is a perspective side view of a drill bit.

For performing procedures within a cannula, a drill generally is used to cut away the bone. The drill bit 128 (FIG. 4) works in conjunction with a drill to provide access to the joint by the immobilization elements. The drill bit can be comprised of a shaft, which may be generally cylindrical, with the drilling portion located at the distal end of the shaft. The diameter of the shaft, however, is less than the diameter of the cannula, such that the drill bit can fit in the passageway formed by the interior surface of the cannula. Referring to FIG. 11, drill bit 128 comprises a shaft 220, turns 222, and point 224. Drill bit 128 at the distal end of the drill bit shaft can be comprised of a plurality of flutes 226 or cutting edges, which assist in the drilling process. In addition, the drill bit can have length markings 228 along the drill bit shaft that assist in determining the depth to which the drill bit has entered the substance being drilled. The proximal end of the drill bit is adapted to fit into a drill. Drill bit 128 can attach to the drill at the shaft or with a chuck. Drill bits can be formed from a metal or metal composite, and are often formed from stainless steel, titanium or tungsten carbide. The diameter of the drill bit is generally slightly less than the diameter of a corresponding immobilization element. For appropriate embodiments, the diameter of the drill bit is less than the inner diameter of the cannula. The drill bit has a sufficient length for attachment to the drill while reaching into the SI joint.

Generally, instructions 130 include necessary labeling as required under FDA regulations. Instructions 130 would further include details for the use of the tools in the immobilization procedure. Instructions 130 can also include appropriate warnings and other desired information, such as contact information and intellectual property information.

Generally, a kit can be distributed with the tools in container 132 with a sterile interior. The sterilization can be performed by any approach in the art, which can be based, for example, on radiation, chemicals and/or sterile process. Some components of the kit are left with the patient, for example, the immobilization element. Other components can be either disposable or can be recycled. Recycled components are generally formed from a material that can be subjected to an appropriate sterilization approach without damage. In general, the shafts of the elements above do not need to have a circular cross section, and other cross sectional shapes can be used.

Immobilization Element

The immobilization element 126 can be comprised, for example, of pins, nails, screws, darts, wedges, shims, cages/connector elements, agglomerated inorganic and/or organic material, or the like, or combinations thereof. These immobilization elements generally can similarly be used in less invasive procedures through a cannula or in more invasive, open surgical procedures. Appropriate delivery approaches can be used for the particular elements. Some of the elements require more or less preparation for delivery. For example, a self-tapping screw with one or more flutes can also be used as an immobilization element, thus obviating the need for drilling.

Figure 12:
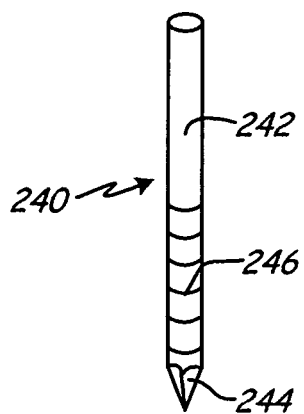
FIG. 12 is a perspective side view of a immobilization pin.
Figure 13:
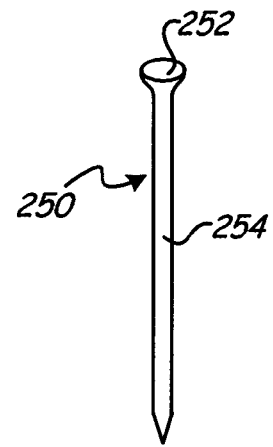
FIG. 13 is a perspective side view of a nail.

Referring to FIG. 12, a pin 240 is shown with a shaft 242, a point 244 and optional gripping element 246. Gripping element can be one or more protruding rings around the circumference of shaft 242, which may or may not be sharp and may or may not be angled to increase gripping. Referring to FIG. 13, nail 250 has a similar structure to pin 240, except that nail 250 includes a head 252 on shaft 254.

Figures 14, 14A:
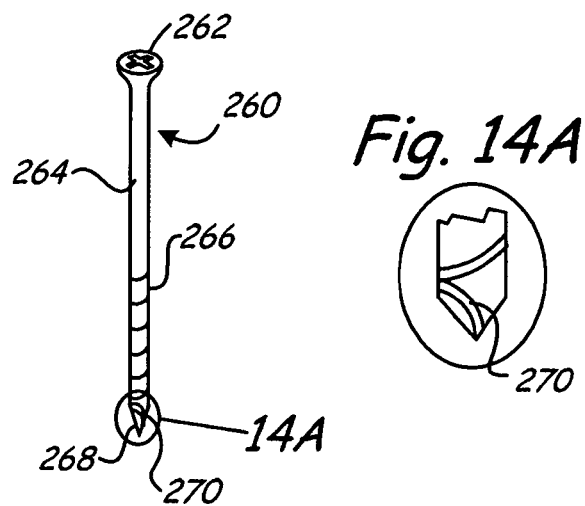
FIG. 14 is a perspective side view of one embodiment of a screw.
FIG. 14A is an expanded, fragmentary perspective side view of an alternative embodiment of the tip of the screw of FIG. 14.
Figure 15:
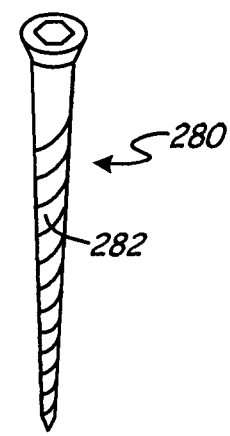
FIG. 15 is a perspective side view of an alternative embodiment of a screw.

Referring to FIG. 14, a screw 260 has a head 262 with a configuration suitable for interfacing with a driver of a corresponding configuration. A wide range of drivers and corresponding heads can be incorporated for these embodiments, including various designs known in the art. Screw 262 has a shaft 264 with threads 266 and a tip 268. In some embodiments, tip 268 (see insert of FIG. 14) has sharp edges or flutes 270 that provide for self tapping of the screw by providing a cutting surface. Threads 266 can be sharp, rounded or square. Sharp threads can provide for cutting of the threads into the surrounding tissue during deployment of the screw into the joint. The threads may or may not have an asymmetric configuration, which may provide for self-locking of the screw. The threads may have a progressively increasing depth toward the tip of the screw. Referring to FIG. 15, a screw 280 has a taper over at least a portion of the screws shaft 282. The taper can be at least about 1 degree and in some embodiments is from about 2 degrees to about 30 degrees. Tapered screw 280 can have other similar features as screw 262.

Pins, nails and screws used as immobilization elements can be formed, for example, from a metal, metal composite, ceramic, polymer or combinations thereof. Also, these elements can have surface texturing to promote anchoring of the elements after insertion. The immobilization element can be formed form a bioresorbable material, such as a resorbable polymer, including for example, polylactic acid or other suitable resorbable polymer. For example, the pins, nails or screws can be formed from stainless steel or surgical grade titanium. A suitable pin, nail or screw generally has a length from about 4 inches to about 10 inches and a width of the shaft for insertion into the joint from about 1.4 millimeters (mm) to about 16 mm. A pin, nail or screw can be hollow, i.e., have a open core, for the passage of a guide pin, such that the immobilization element can be placed as guided by the guide pin, and the shaft of these elements may or may not have a circular cross section.

Figure 16A:
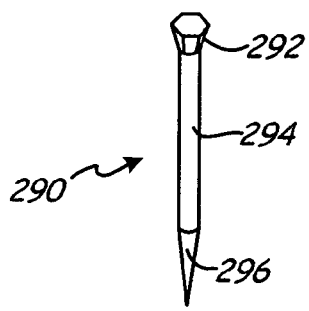
FIG. 16A is a perspective side view of a dart.
Figure 16B:
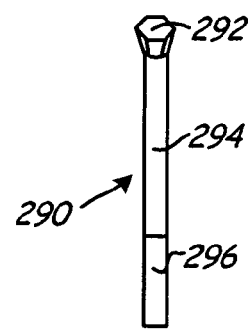
FIG. 16B is a perspective front view of the dart of FIG. 16A.
Figure 17A:
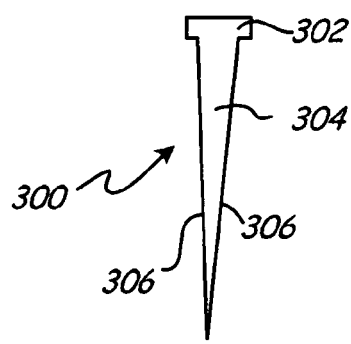
FIG. 17A is a perspective side view of a wedge.
Figure 17B:
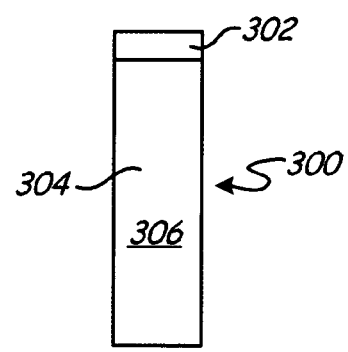
FIG. 17B is a perspective front view of the wedge of FIG. 17A.
Figure 18A:
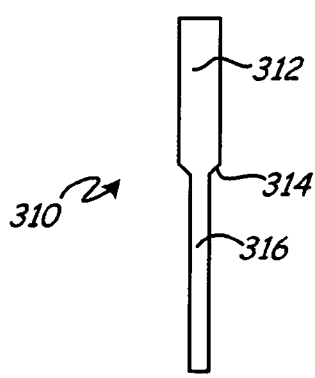
FIG. 18A is a side view of a shim.
Figure 18B:
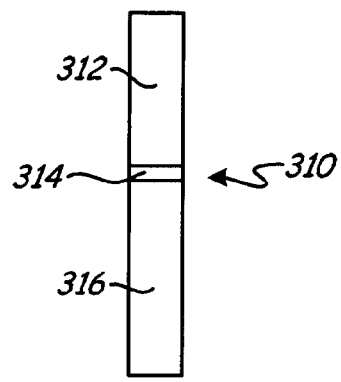
FIG. 18B is a front view of the shim of FIG. 18A.

A dart may have a similar shape at the proximal end as a pin or nail, but the dart has a flattened shape at its distal end. Referring to FIGS. 16A and 16B, dart 290 has a head 292, shaft 294 and a tip 296. Tip 296 can have a wedge shape or other similar shape, such as an arrow head shape, or the like. Wedge 300 is depicted in FIGS. 17A and 17B. Wedge 300 has a head 302 and wedge portion 304. Faces 306 of wedge 300 may or may not be planar, and the front view of faces 306 may or may not be rectangular. Shim 310 is depicted in FIGS. 18A and 18B. Shim 310 has a first portion 312, a taper 314 and a thin insertion portion 316. Many variations on the particulars or the shim are possible, and combinations of the features of the wedge and shim can be used to form an immobilization element. Also, darts, wedges and shims can have surface texturing and/or protrusions to accentuate the anchoring of the elements. Darts, wedges and shims can be formed from the same materials as pins, nails and screws, and generally have similar dimensions. Darts, wedges and shims generally have a thickness for insertion into the joint from about 1.4 millimeters (mm) to about 16 mm.

The anchor elements, e.g., pins, nails, screws, dart, shim, and/or wedge, can be further connected to plates, nuts, cages and other connectors that can form an immobilization cage. For example, a plate can connect a plurality of connector elements with a head anchoring the plate/cage. In some embodiments, a plate, cage or the like is implanted in an open procedure. Such a connector can be formed from comparable materials as the other immobilization elements. Anchor elements can be delivered with an appropriate anchor deployment tools, such as a driver, a mallet, a tap, a hammer or the like. Appropriate extensions can be used to extend the anchor deployment tool into a cannula to effectuate the deployment. Deployment tools generally are formed from a material suitable for sterilization for reuse.

In addition, suitable immobilization elements include delivered compositions that harden within the joint. Suitable compositions include, for example, metal powder, such as powders of titanium or titanium compositions with appropriate particle size, can be formed into composites, for example, with rigid polymers to form desired immobilization elements. In addition, synthetic bone materials and/or sterile bone materials, either allograft or xenograft materials, can be used to form the implantation elements. Suitable synthetic bone material includes, for example, coral and calcium compositions, such as hydroxyapatite, calcium phosphate and calcium sulfite. These compositions can be anchored with suitable polymers and/or adhesives. Suitable adhesives include, for example, surgical adhesives, such as cyanoacralate adhesives (such as 2-octyl cyanoacrylate, Dermabond™, from Ethicon Products), fibrin glue (such as Tissucol® from Baxter) and mixtures thereof. Suitable biocompatible urethanes and epoxies can similarly be used. These compositions can be delivered in suitable amounts with a syringe or the like.

The immobilization elements can be delivered along with a biologically active agent to act together to yield a desirable event with the immobilized joint. Delivery of bioactive agent can be performed, for example, by coating the immobilization device with the bioactive agent, combining the bioactive agent with a material incorporated in the immobilization agent and/or delivering the bioactive agent in the vicinity of the immobilization device. Specifically in some embodiments, a bioactive agent can be incorporated into the material of the immobilization agent for gradual elution into the joint. In particular, if the immobilization device comprises a polymer, the bioactive agent can be combined within the polymer. The bioactive agent then elutes into the patient for inducing the desired effect. The composition of the polymer, such as chemical composition and molecular weight, can be selected to yield a desired elution rate.

Alternatively, the bioactive agents can be coated on the surface of the immobilization element. To coat the immobilization device with the bioactive agent, the device can be dipped in a composition comprising the bioactive agent, sprayed with a composition comprising the bioactive agent, painted with the bioactive agent, and/or coated with other processes, such as those generally known in the art. If the coating composition comprises a solvent, the solvent can be allowed to evaporate after applying the coating composition. The bioactive agent can be applied alone as a coating composition or with another agent to control the elution of the agent. The agent can be applied from a solution with a solvent that can evaporate following the application of the coating solution. Also, the bioactive agent can be combined with a control release agent, such as a biodegradable polymer that gradually releases the bioactive agent. Biocompatible, biodegradable polymers are known in the art, such as polylactic acid, poly(glycolic acid) and copolymers and mixtures thereof. A binder may or may not be included to control the elution from the coating.

Suitable biologically active agents include, for example, bone morphogenic protein (BMP) and suitable cytokines. BMP is involved in formation and healing of bone related tissue, including bone, cartilage and tendon. Suitable cytokines include, for example, human chemokine alpha 2, which is effective to stimulate bone marrow growth.

Furthermore, the bioactive agent can be injected or otherwise delivered in the vicinity of the immobilization device. The bioactive agent can be combined with a suitable biocompatible carrier, such as commercially available buffered saline.

Procedure

A variety of procedures can effectively make us of the tools and immobilization elements described herein. The procedures can be open procedures or less invasive procedures performed through a cannula. The procedures are directed to the objective of immobilizing the SI joint upon a determination that such a result is indicated. An immobilization element is placed within the SI joint in contact with adjacent tissue. In general, it can be desirable to remove the top layer of the bone at the immobilization point prior to immobilization to expose an inner portion of the bone to stimulate the healing process that can promote bone formation at or around the immobilization element. This exposure of the bone can be performed using drilling, cutting, scraping or the like.

Open procedures involve an incision that exposed the joint to visual observation. Such an incision generally would be at least several inches in length. Tools, such as conventional retractors and the like, can be used to hold the incision open. Due to the extent of the cutting of muscles, a significant recovery time is generally needed to facilitate the recovery period.

Less invasive procedures involve small incisions generally no more than four cm across and in some embodiments no more than 2.5 cm across. These procedures can make use of a cannula or the like to guide the procedure. The cannula can be placed with the use of a trocar device, as described above. In particular, the trocar inserted within the cannula is guided through the small incision to the location of the SI joint. The trocar is removed once the cannula is in position, and the remaining immobilization steps can be performed through the cannula. In particular, any preparation of the immobilization site involving cutting, drilling and the like can be performed through the cannula.

Generally, a guide pin can be used to orient performance of a less invasive procedure. Placement of the guide pin can be based on an appropriate image of the patient. Additional imaging can be performed to verify desired placement of the guide pin with the pin in place. An incision is made around the guide pin. While the guide pin can be used for open or less invasive procedures, if a less invasive procedure is performed, the cannula is generally placed around the guide pin. The cannula can be positioned using a cannulated trocar that fits over the guide pin. Once the cannula is in place, the site can be prepared for immobilization. For example a cannulated drill bit can be used to drill around the pin position. The desired immobilization element can then be placed in the SI joint at the pin position. The pin may or may not be removed following the delivery of the immobilization element. The pin may be cut down if desired. Following deployment of the immobilization element(s), the incision is then closed.

A series of immobilization elements can be placed along the joint using either an open procedure or a set of less invasive procedures. For example, the series of immobilization elements can be placed in a row in the joint. In this way, two, three, four or more immobilization elements can be placed along the SI joint.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. A method for immobilizing a patient's sacroiliac joint through a passageway provided by an extra-articular recess into the sacroiliac joint wherein the sacroiliac joint and the extra-articular recess are formed by a surface of an ilium bone and a surface of a sacrum bone, the method comprising inserting an immobilization/fusion element into the sacroiliac joint between the ilium and the sacrum bones through the extra-articular recess and thereby driving apart the surfaces of the ilium and sacrum bones that form the sacroiliac joint and adjoining surfaces of the extra-articular recess, wherein the element is inserted through a cannula, over a pin, or both, that is placed through an incision formed in the patient to immobilize the sacroiliac joint.

2. The method of claim 1 further comprising drilling a region at the sacroiliac joint through the cannula.

3. The method of claim 2 wherein the drilling step is performed using a drilling guide.

4. The method of claim 1 further comprising placing a guide pin through the cannula.

5. The method of claim 4 wherein the guide pin is place using real time imaging.

6. The method of claim 1 further comprising positioning the cannula with a trocar.

7. The method of claim 1 further comprising placement of a second immobilization/fusion element within the opening of the sacroiliac joint.

8. The method of claim 1 wherein the immobilization/fusion element is associated with a bioactive agent.

9. The method of claim 8 wherein the bioactive active agent comprises bone morphogenic protein or a cytokine effective to stimulate bone marrow growth.

10. The method of claim 1 wherein the immobilization/fusion element comprises a screw.

11. The method of claim 10 wherein the screw is a self-tapping screw.

12. The method of claim 1 wherein the immobilization/fusion element comprises an unthreaded pin.

13. The method of claim 1 wherein the immobilization/fusion element has a central channel and is inserted over a guide pin.

* * * * *

UNITED STATES PATENT AND TRADEMARK OFFICE
CERTIFICATE OF CORRECTION

| | | |
|---|---|---|
| PATENT NO. | : 7,648,509 B2 | Page 1 of 1 |
| APPLICATION NO. | : 10/797481 | |
| DATED | : January 19, 2010 | |
| INVENTOR(S) | : John G. Stark | |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 267 days.

should read (*) Notice: Subject to any disclaimer, the term of this patent is extended or adjusted under 35 U.S.C. 154(b) by 359 days.

Item (56), References Cited, U.S. Patent Documents, delete "6,562,049 B1 5/2003 Norlander et al." and insert --6,562,046 B2 5/2003 Sasso--.

Signed and Sealed this

Eighteenth Day of May, 2010

David J. Kappos
*Director of the United States Patent and Trademark Office*